United States Patent
Laser (10) Patent No.: US 7,976,459 B2
(45) Date of Patent: Jul. 12, 2011

(54) PORTABLE ENDOSCOPE FOR INTUBATION

(75) Inventor: Vadim Laser, Maineville, OH (US)

(73) Assignee: Intra L.L.C., Cincinnati, OH (US)

( * ) Notice: Subject to any disclaimer, the term of this patent is extended or adjusted under 35 U.S.C. 154(b) by 937 days.

(21) Appl. No.: 11/873,562

(22) Filed: Oct. 17, 2007

(65) Prior Publication Data

US 2008/0091064 A1    Apr. 17, 2008

Related U.S. Application Data (60) Provisional application No. 60/829,763, filed on Oct. 17, 2006.

(51) Int. Cl.
*A61B 1/05* (2006.01)
*A61B 1/06* (2006.01)

(52) U.S. Cl. ........ 600/109; 600/110; 600/129; 600/176; 600/179

(58) Field of Classification Search .................. 600/109, 600/129, 130, 110, 179, 176; 348/76, 68
See application file for complete search history.

(56) References Cited

U.S. PATENT DOCUMENTS

| | | | |
|---|---|---|---|
| 4,919,114 A * | 4/1990 | Miyazaki | 600/110 |
| 5,718,663 A * | 2/1998 | Wulfsberg | 600/176 |
| 6,095,970 A * | 8/2000 | Hidaka et al. | 600/110 |
| 6,387,043 B1 | 5/2002 | Yoon | |
| 6,543,447 B2 | 4/2003 | Pacey | |
| 6,655,377 B2 | 12/2003 | Pacey | |
| 6,692,431 B2 | 2/2004 | Kazakevich | |
| 6,929,600 B2 | 8/2005 | Hill | |
| 7,042,487 B2 | 5/2006 | Nakashima | |
| 7,063,663 B2 | 6/2006 | Kazakevich | |
| 7,662,094 B2 * | 2/2010 | Iddan | 600/176 |
| 7,773,122 B2 * | 8/2010 | Irion et al. | 348/222.1 |
| 2002/0080248 A1 | 6/2002 | Adair et al. | |
| 2003/0050534 A1 | 3/2003 | Kazakevich | |
| 2003/0089776 A1 * | 5/2003 | Hennick et al. | 235/454 |
| 2004/0111012 A1 * | 6/2004 | Whitman | 600/179 |
| 2004/0225189 A1 * | 11/2004 | Kimoto et al. | 600/160 |
| 2006/0004258 A1 | 1/2006 | Sun et al. | |
| 2006/0183977 A1 * | 8/2006 | Ishigami et al. | 600/179 |
| 2006/0264709 A1 * | 11/2006 | Fujimori et al. | 600/130 |
| 2006/0276693 A1 | 12/2006 | Pacey | |
| 2006/0281972 A1 * | 12/2006 | Pease et al. | 600/109 |

* cited by examiner

*Primary Examiner* — John P Leubecker
(74) *Attorney, Agent, or Firm* — Hasse & Nesbitt LLC; Daniel F. Nesbitt (57) ABSTRACT

A portable, low power, low cost, endoscope having a removable probe with a miniature digital CCD imager, single white LED illuminator and an imaging lens on the distal end and a miniature multi pin connector on the proximal end; both ends connected with a multi trace flexible circuit hidden inside of the protecting flexible sleeve; and a full color LCD monitor and associated image signal processing electronics and powered by the small battery cells.

17 Claims, 7 Drawing Sheets

HEAD ASSEMBLY

Flowchart of the Endoscope process control

PORTABLE ENDOSCOPE FOR INTUBATION

CROSS-REFERENCE TO RELATED APPLICATIONS

This application claims the benefit of U.S. Provisional Application 60/829,763, filed Oct. 17, 2006, the disclosure of which is incorporated herein by reference.

FIELD OF THE INVENTION

This invention is concerned with the devices used for assisting a medical practitioner during endotracheal intubation procedure.

BACKGROUND OF THE INVENTION

The endotracheal intubation is a commonly used procedure during which a semi rigid plastic tube, called endotracheal tube, is inserted into a patient's trachea through the open mouth. Frequently a laryngoscope is used to view the throat area while the tip of the endotracheal tube advances toward the vocal cords. This procedure is not a trivial one especially in the inconvenience of emergency situations and with the patients having various irregularities and complications in the throat and neck areas. During the last five to ten years many researches and physicians advocated use of endoscopes during the intubation procedures. The tip of the flexible shaft of an endoscope is inserted into the endotracheal tube and temporarily secured near the distal end of it. Depending on the type of an endoscope used, a practitioner performing intubation can see the area in the immediate vicinity of the distal end of he endotracheal tube either on the video screen of a monitor or looking in the ocular of a simpler endoscope. It is quite obvious that such use of an endoscope reduces number of traumas and helps to ease and speed up the intubation process. Many existing endoscopes can be used for such application. However, a typical medical endoscope is an expensive and bulky instrument, utilizing powerful light sources and fiber optic bundles for delivery of light and/or images. There is a need for a portable and inexpensive endoscope suitable for use in the operating rooms as well as, emergency situations, and anywhere an endotracheal intubation needs to be performed. The attempts to develop a portable and less expensive endoscopes, particularly convenient for endotracheal intubation have been made. The U.S. Pat. Nos. 7,042,487 and 6,929,600 teach how to make a less bulky and less expensive endoscopes yet they failed to get rid of fiber optic bundles and external light sources. This invention discloses the way to do just that, how to construct a low cost and portable endoscope that can be conveniently used for endotracheal intubation in any situation.

The endoscopes have been useful tools in the medical field for many decades. Doctors and paramedics use them for diagnostic purposes as well as in combination with the surgical tools during operations. There are endoscopes that combine imaging functions with the tubular channels for moving liquids and gases in and out of body and channels for controlling the surgical tools. In spite of being well known tool, the endoscopes find new useful applications. One of such relatively new applications is providing assistance during intubation procedure. Benefits of the endoscopes during intubation have been demonstrated in the scientific medical publications during the last 5-10 years. The endoscopes currently known are rather bulky and expensive. High price, a suitcase-type dimensions at best, and large power requirements preclude use of the endoscopes in the battlefield and the every day typical ambulance situations. There is a need for a low cost, small, light weight endoscope that medical personal can use equally well in the traffic accidents on the streets and in the operating rooms.

The main function of an endoscope is to make available to a person a viewable image of the scene located in front of the inserted probe end of the flexible shaft. This can be accomplished in one of two ways. First, traditional way offers a solution through the use of a coherent bundle of light-conducting fibers combined with the image projecting lenses. The fibers bring forward the image of the scene, which is illuminated by the light brought by a few insulated fibers inside of the body from the powerful external light source. This image then either viewed by the eye through an eyepiece lens or projected on a TV camera and viewed from the TV monitor. This concept results in an endoscope system that is complicated, expensive and bulky. The typical light source is a halogen or an arc lamp of 50 to 75 watts.

Conventionally, many fibers bundled together with a charge couple device (CCD) used to take pictures to form an endoscope, which is used to penetrate hollow organs (e.g., stomach, large intestine and trachea) to get tissue images for determining the type and development degree of diseases. Light from a light source is transmitted through the fibers to illuminate a tissue of the human body. The reflected light is transmitted back via the fibers to the CCD for formation of an image displayed on a screen. The diameter of common fibers is smaller than 100 microns. In order to observe an image region from several millimeters to several centimeters, it is necessary to bundle a considerable number of fibers to obtain an image with a sufficient resolution. Moreover, the size of a typical CCD image sensor is generally large. The above fiber-type endoscope has the disadvantages of high price and complexity and difficult assembly and maintenance. Because, the above fiber-type endoscope has a high price, it is usually used repetitively for many times so that infection may occur due to difficult sterilization.

In order to solve the above problems of the fiber-type endoscope, U.S. Pat. No. 6,387,043 discloses a transmission type endoscope, wherein a complementary metal-oxide semiconductor (CMOS) image sensor replaces the CCD. A transmission type endoscope applies to common surgical laporoscopic operations. The transmission type endoscope comprises a penetrating member, a hollow portal sleeve connected with the penetrating member, and a main body at the rear end. A penetrating member has a sharp front end for penetrating tissues. This penetrating member is equipped with two imaging CMOS cameras, one inside the member and another outside of it. Each of these cameras has and LED light source for illumination, object lens for projecting images, and CMOS image sensors for converting optical signals into electric signals.

U.S. application Ser. No. 2002/0080248 A1 discloses an endoscope of another type. Light from the light source and reflected light present via fibers in conventional endoscopes. In this disclosure, the illumination way of the light source is reserved. Only the CCD image sensor is replaced with a CMOS image sensor. This endoscope comprises a flexible sleeve, a handle, and a control box. An optical imaging device is installed at the front end of the flexible sleeve. The optical imaging device comprises from outside to inside an outer cover, optical fibers, and an image sensing device. An optical lens is disposed at the front end of the image sensing device. A CMOS sensor is disposed behind the image sensing device. The CMOS sensor can be a circular or a square image sensor. The handle is used for convenient maneuvering of the endoscope. The control box provides electric power and has an image processing board for processing image signals.

Although the above two disclosures address the problems of fiber-type endoscopes and avoid the situation of using too many fibers, there remains a need to further develop a solid state image sensor with a small size and low power requirement.

The other, more feasible, method constructs an endoscope with an image sensor placed near the front end of the flexible probe. This is possible because the solid state image sensors are becoming available in sufficiently small packages. Having an image sensor at the front end eliminates or reduces the signal losses and simplifies construction. The availability of small size and high efficiency white light emitting diodes (LED) in combination with high sensitivity image sensors allows construction of a simple and elegant endoscope system, such as described in US Application Publication 2006/0004258, by Wei-Zen Sun, et al. In this publication a CMOS image sensor is installed behind the light emission devices. Light reflected by the human body is focused by an object lens onto the CMOS image sensor, which converts the optical signal into an electric signal. The electric signal is processed by the image sensor drive circuit board, which is positioned immediately behind the image sensor, and is then sent to the display device via electric wires for real-time monitoring of images of the human body tissue. The lens has a very restricted view angle due to the obstruction of the multiple LED illuminator board positioned in front of the lens. The lens can see the space in front of it through the small aperture made in the center of the housing integrated with the light source module. The necessity of the drive circuit board and multi-LED illuminator module prohibit construction of a small diameter endoscope probe.

Thus, there remains a need for further improvements in portable endoscopes in the use.

SUMMARY OF THE INVENTION

The present invention provides a portable video endoscope that is small in size and light in weight, and suitable for assistance during intubations, and in particular endotracheal intubation.

The invention also provides a portable video endoscope that has low cost.

The invention further provides a portable endoscope with an easily detachable and replaceable probe, capable of being disinfected for multiple reuses.

The invention still further provides a portable endoscope that has inherently high reliability due to absence of components statistically vulnerable to failure.

The invention also provides a portable endoscope that can be powered by widely available disposable or rechargeable battery cells.

The invention also provides a portable endoscope with a flexible probe of sufficiently small diameter and suitable for insertion inside of the variety of endotracheal tubes.

The invention still further provides a portable endoscope having an improved field of view without sacrificing image quality.

The present invention provides a portable endoscope suitable for aiding during endotracheal intubation comprising: a digital imaging probe module, an in-line probe controller module, and a display and control module. The present invention also provides a digital imaging probe comprising: a CCD frame transfer type image sensor in a micro ball grid array packaging, a wide angle imaging lens positioned in front of the sensitive area of the sensor, an LED illuminator positioned in the space in front of the storage area of the sensor and next to the imaging lens, an optically clear window positioned immediately in front of both the lens and the LED illuminator, a light blocking separator positioned between the lens and the LED illuminator, a flexible circuit carrying the image sensor and having an extension with the LED on its tip on one end and the multi pin connector on the other end, a cylindrical enclosure that holds all the above elements together in their relative positions and is impermeably connected to the flexible sleeve that encloses the flexible circuit.

The present invention also provides a digital imaging probe having a cylindrical enclosure and comprising: a CCD image sensor having a sensitive area and a storage area, a wide angle imaging lens positioned in front of the sensitive area of the sensor; an LED illuminator positioned in the space in front of the storage area of the sensor and next to the imaging lens; an optically clear window positioned immediately in front of both the lens and the LED illuminator, and having an inner surface; a light-impermeable separator positioned between the lens and the LED illuminator, and extending to the inner surface of the window; and a flexible electrical circuit having a first end in electrical communication with the image sensor and with the LED, and having a second end consisting of an electrical coupling.

A useful improvement in an intubation procedure is for an endoscope with a wide angle of view. The wide angle is useful for viewing the tip of the intubation tube and the body tissue in front of and around the tube, both located in the immediate proximity of the lens. If the viewing angle is not wide enough it is difficult to make a quick judgment on the exact position of the tip of the endotracheal tube. If the viewing angle is wider than necessary, then a large portion of the screen contains an image of the inner wall of the tube, which has no useful information and waists valuable and limited resolution of the monitor screen. The desired view angle for the intubation endoscope is no less than 80 angular degrees, more typically is no less than 90 degrees and no more than 120 angular degrees, and more typically is no more than 110 angular degrees, while the desired angle typically is 100 degrees. There are certain obstacles that cause difficulties to providing such wide-angle feature. The wide-angle objective lens and the wide-angle illuminating LED must coexist in the very tight quarters of the endoscope head. To improve the compatibility with the most commonly used endotracheal intubation tubes, the outside diameter of the endoscope probe typically does not exceed 6 mm. The end of the probe has a transparent window, sealed inside the probe enclosure. The objective lens and the illuminating LED are placed close to the window to take advantage of their wide-angle geometry and obtain a wide view angle.

However, the window in the immediate vicinity of the lens and LED creates a direct optical crosstalk between them, which reduces the contrast and can blind the sensor with the specular reflections of the LED light from the window. A wide viewing angle without the artifacts of the optical crosstalk is provided by placing a barrier, such as a thin, opaque light separator, between the illuminating LED and the objective lens. Extending the separator all the way to the inner surface of the window eliminates the undesired crosstalk from the LED. Such separator can be made of black vinyl film, black anodized aluminum foil, or other opaque material.

Due to a very small space available in the head of the endoscope probe, it is desirable that a single miniature LED provides an amount of light sufficient for performance of the imaging sensor. High sensitivity is one important criteria for selection of the image sensor. The other desired requirements are: compact size, low cost, and placing the light sensing area of the sensor significantly offset from the center of the probe head. One type of the sensor that meets these requirements is a CCD image sensor with frame transfer architecture. A CMOS sensor can also be used, though, in spite of the progress made in the CMOS sensor technology, the best CCD sensors are more sensitive. The frame transfer architecture, where the image sensing area is separate from the image storage area provides improved performance in terms of sensitivity and signal-to-noise ratio due to having largest possible fill factor of the light sensitive area to the total area of a pixel. Having the sensing and storage areas coexisting on the same plane of the chip surface, the imaging area is offset from the center of the chip. This, in turn, provides the room needed for placing the illuminating LED next to the objective lens. Such configuration assures a compact juxtaposition of the lens and illuminator inside the small cylindrical enclosure of the probe head.

For example, one embodiment of the endoscope probe built according to the disclosed drawings has a maximum outside diameter of 5.5 mm. A flexible probe of such small maximum head diameter is well suited for intubation procedures. These digital-output sensors are low cost, sensitive, and small in size, and in plentiful supply, owed to their original development and production for the very large and price competitive cellular phone market. The proposed endoscope system utilizes the frame transfer miniature CCD image sensor, the DSP CCD processor and miniature surface mount white LED. In addition to the advantage of having a field transfer architecture, which assures the best sensitivity in the visible spectrum, the proposed solution also takes advantage of the ability to take images by the sensor with a reduce frame rate but display those images with a standard TV video rate, free of the image flicker. This provides an additional increase in sensitivity, which makes possible the use of a single miniature surface mounted, white LED for illumination. The miniature CCD frame transfer image sensor has wonderful features useful for the construction of the small diameter wide angle endoscope probe. In order to be small in size, the sensor is stripped of auxiliary electronics, and provided with a number of control signals and supply voltages, typically prepared by a corresponding controller integrated circuit, named "CCD DSP. There is a practical limit of how far the CCD DSP can reside from the image sensor. It has been determined empirically, that with the use of a fourteen-trace flexible circuit approximately 3 mm wide the distance between the CCD image sensor and its CCD DSP controller can extend up to about 0.5 m (20 inches). Such distance allows construction of a removable probe of comfortable length. Such probe comprising: 1) at its distal end, a digital imaging probe module with the CCD image sensor, lens and single LED; 2) at its proximal end, a miniature multi-pin connector; and 3) a cable comprising a flexible electronic circuit that is enclosed within a protective sleeve and connects the CCD image sensor and the multi-pin connector. The in-line probe controller module of miniature dimensions comprises a miniature connector that mates with the multi-pin connector of the digital imaging probe module, a sealed plastic box that houses the CCD DSP-based electronics, and a digital cable that attaches to and connects the sealed plastic box to the display and control module. Having the in-line probe controller module allows a probe of convenient length to be replaceable and serves the function of housing the necessary CCD DSP electronics away from the tight space of the probe module.

DETAILED DESCRIPTION OF AN EMBODIMENT OF THE INVENTION

Figure 1:
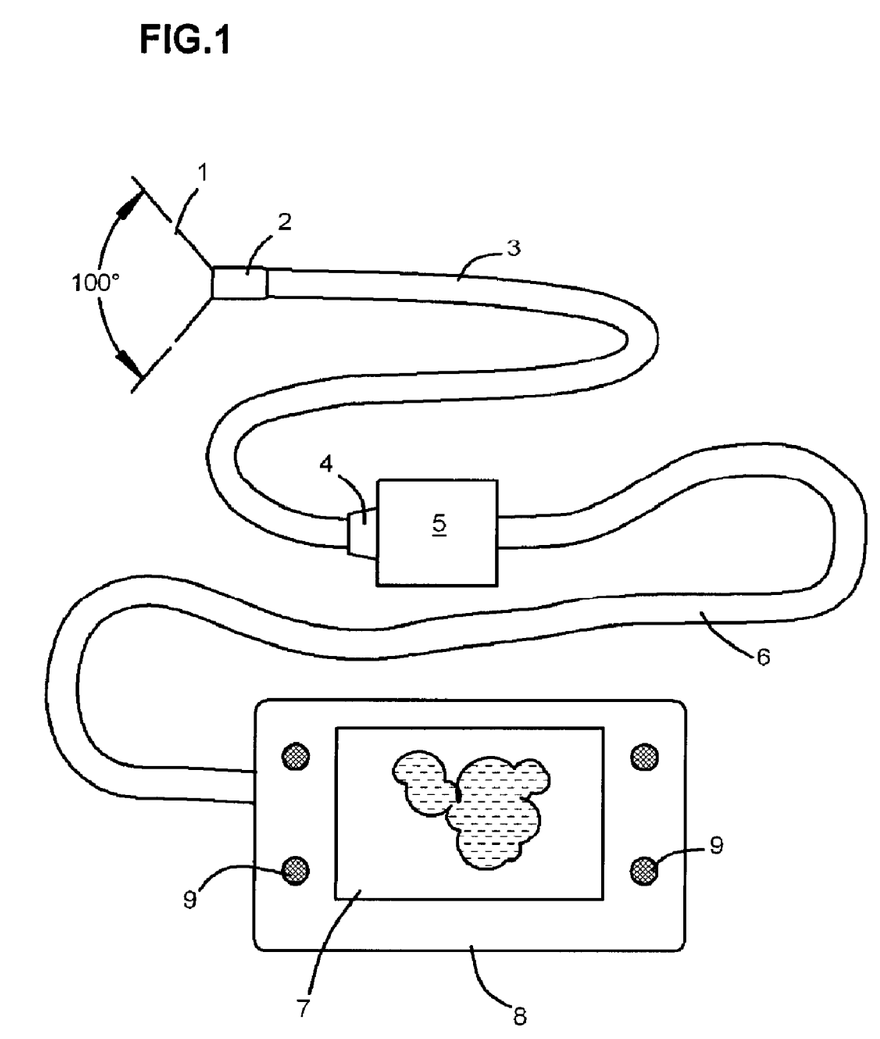
FIG. 1 shows the main component modules of a portable electronic endotracheal endoscope apparatus according to the present invention, including a digital imaging probe module, an in-line probe controller module, and a display and control module.

The FIG. 1 shows the main components of an embodiment of the invention. The flexible probe consists of the imaging head 2 with the viewing angle 1 of 100 degrees, the flexible circuit enclosed into the plastic sleeve 3 and the miniature 14-pin connector 4. The connector 4 is plugged into and electronically communicates with the small in-line control box or enclosure 5 that houses the image sensor controller (not shown). The in-line probe controller box 5 is connected via the second flexible multi-line cable 6 comprising control wiring 42 to the control and display unit 8. The control and display unit 8 has a 3.5" color TFT LCD video display panel 7, knobs 9 for controlling the power and brightness, battery cell compartment accessible from the back and an electronic hardware positioned inside the enclosure.

Figure 2:
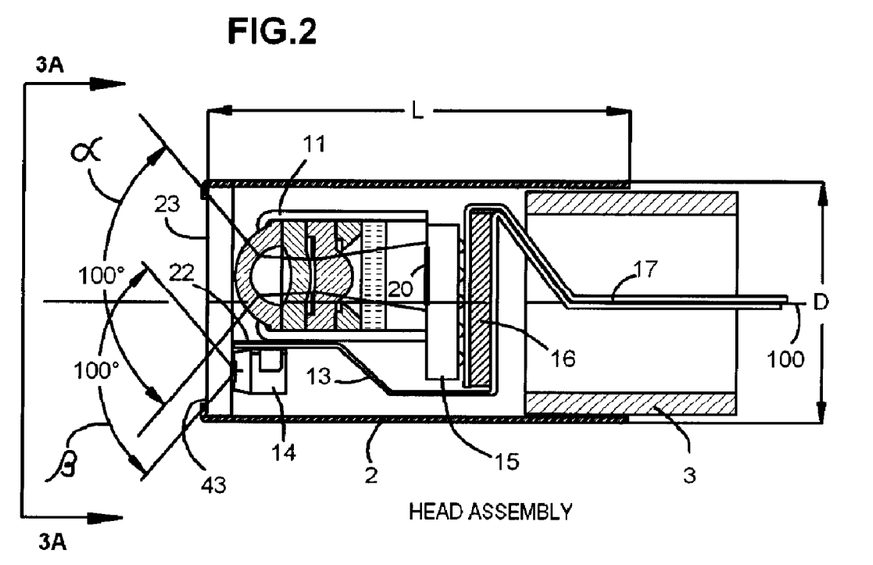
FIG. 2 shows a cross sectional view along the longitudinal axis of the imaging head of the digital imaging probe module.

The longitudinal cross section of the head of the probe, presented on the FIG. 2, shows how the proposed invention resolves the conflicting requirements of the all imaging related components to be enclosed into a small diameter housing and at the same time providing a wide angle of illumination and viewing of the scene. The thin wall cylindrical stainless tube 2 has a 5.5 mm outside diameter D and a 9 mm total length L. It has a small inward flange 43 at the front end, which prevents a transparent sapphire window 23 from falling out. The window 23 and the tube 2 are bonded reliably to form a liquid seal at their contact. Immediately behind the window 23, a wide angle lens 11 is positioned against the image sensor 15 in such a way that it is centered against the sensitive area 20. The lens system 11 has an outside diameter of 3 mm. It can be obtained from Applied Image Group of Tucson, Ariz. The lens is offset from the longitudinal axis 100 of the tube 2, leaving enough room for the miniature surface-mounted white LED 14. The leading surface of the LED 14 is also positioned immediately against the window 23. The white LED part number NxSW008B is manufactured by Nichia Corporation. LEDS consuming less than 100 mW are typical and preferred. Both, the lens 11 and the illuminating LED 14 have their respective optical reception angle α and illumination angle β equal to about 100 degrees each. The drawing shows that both these angles are not constricted by any obstacles and fit into the available aperture of the window 23. The white LED 14 is mounted on and is powered by the extension 13 of the flexible circuit 17. The flexible circuit 17 typically is made of the thin polyamide films such as Kapton® (registered trade name of Du Pont) with the cold-rolled copper traces trapped in between. In the preferred embodiment the combined thickness of the two Kapton films is 25 microns. Such thin film is translucent to the visible light especially of yellow color. In order to block the light from being emitted through the thin film of the flexible circuit, the back surface of the flexible circuit extension 13 is separated from the other components of the probe with a light-blocking separator 22, which can be made of a black vinyl film, black anodized aluminum foil or other suitable light blocking film or paint. Such black film extends up to the inner surface of the window 23 and assures absence of a direct crosstalk between the LED 14 and the lens 11. The image sensor 15 has a micro ball grid array packaging and is soldered on the pads of the long and narrow flexible circuit 17 near its distal end. The flexible circuit 17 is protected from the environment by the plastic sleeve 3. The sleeve 3 and the enclosing tube 2 are joined together with a water-tight permanent connection, such as an adhesive bond or a mechanical crimp.

Figure 3A:
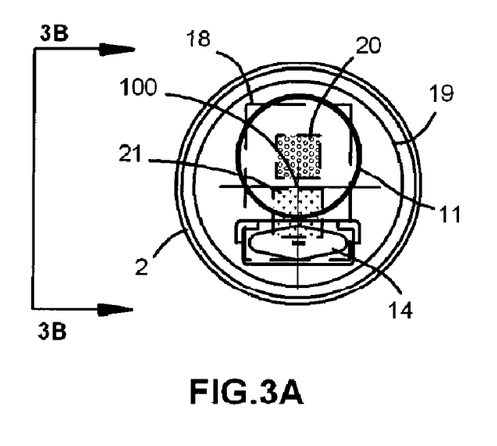
FIG. 3A shows a front elevation view of the digital imaging probe module, taken from line 3A-3A of FIG. 2.
Figure 3B:
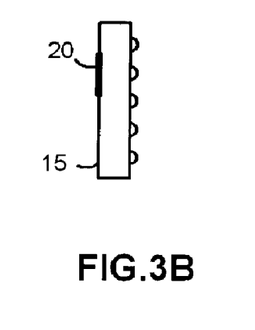
FIG. 3B shows a side elevation view of the digital imaging probe module, taken from line 3B-3B of FIG. 3A.

The FIG. 3 is a drawing that illustrates the advantage of the frame transfer CCD image sensor in the endoscope application. The image sensing area 20 allows the lens 11 to be off center of the axis 100 of the housing enclosure 2, thus providing sufficient room for the LED 14. The item 21 is the image storage area, which must have some space on the silicon chip. It causes the sensing area 20 to be significantly off center of the chip. The particular image sensor that meets the discussed requirements is a part number LC99267FSB manufactured by Sanyo Electronics. The associated CCD DSP controller component has part number LC99807-CYEB-GB, also made by Sanyo Electronics.

Figure 4:
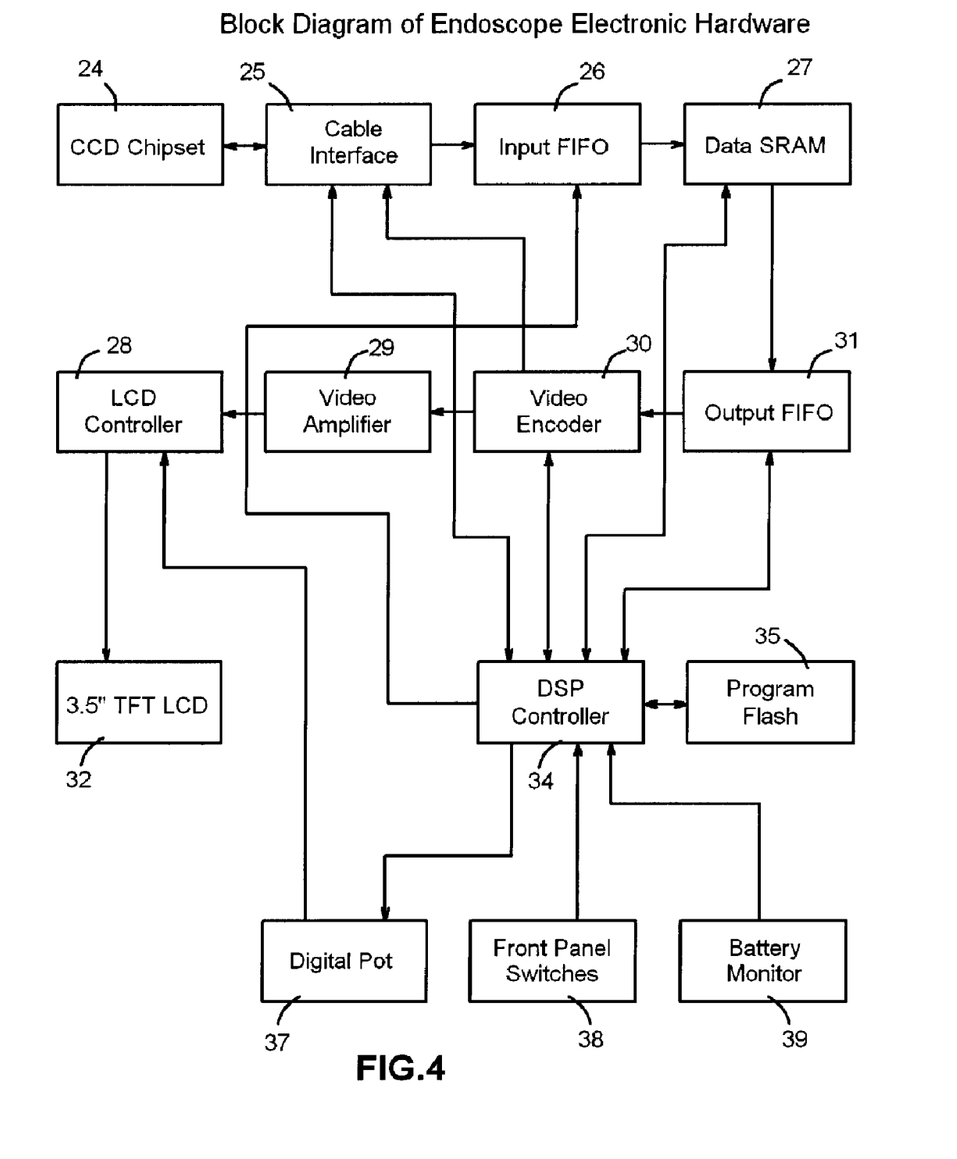
FIG. 4 shows an electronic hardware block diagram of the portable endoscope apparatus.
Figure 5:
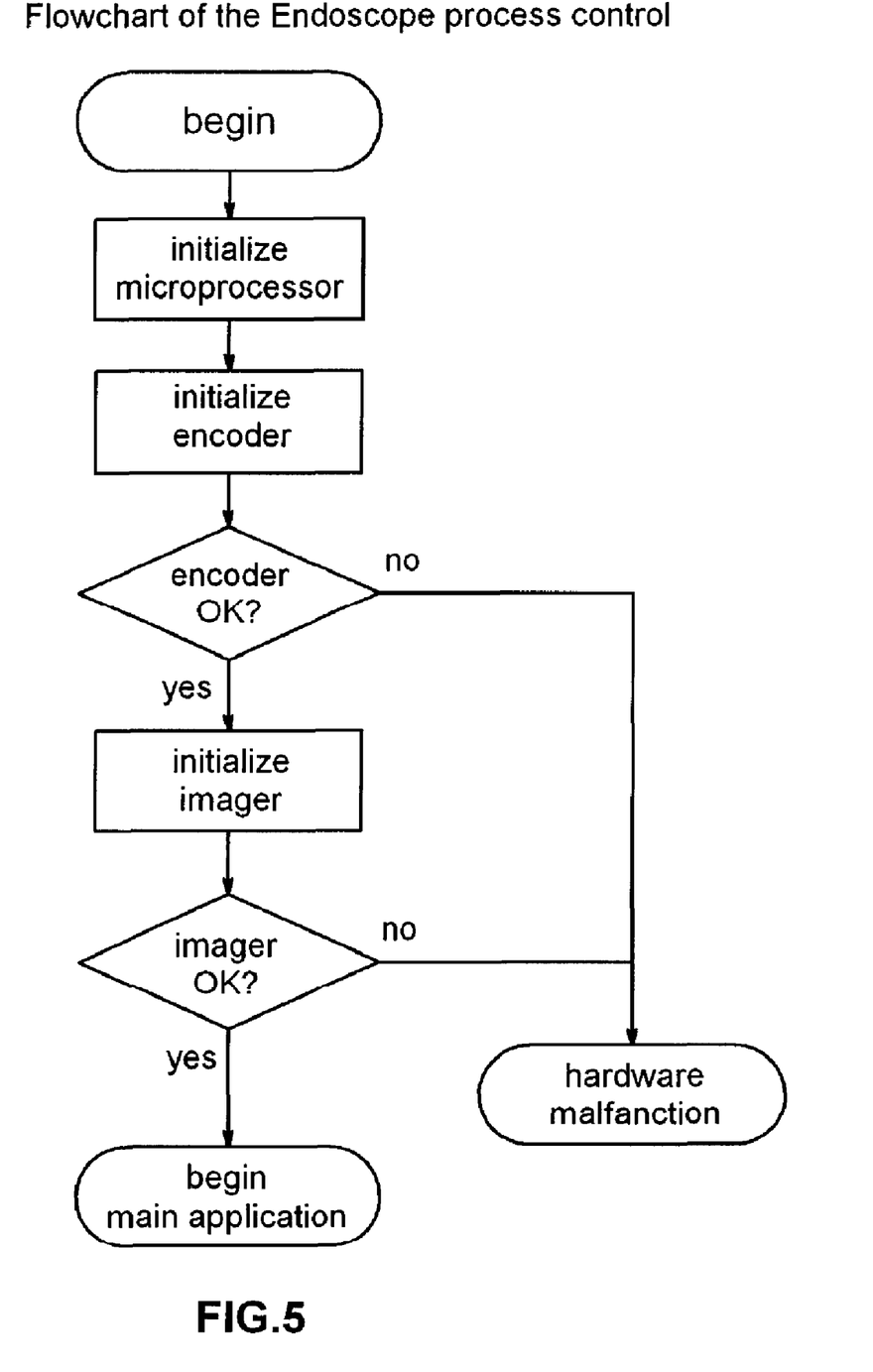
FIGS. 5, 6, 7 and 8 present collectively the process control flow chart of the portable endoscope apparatus.
Figure 6:
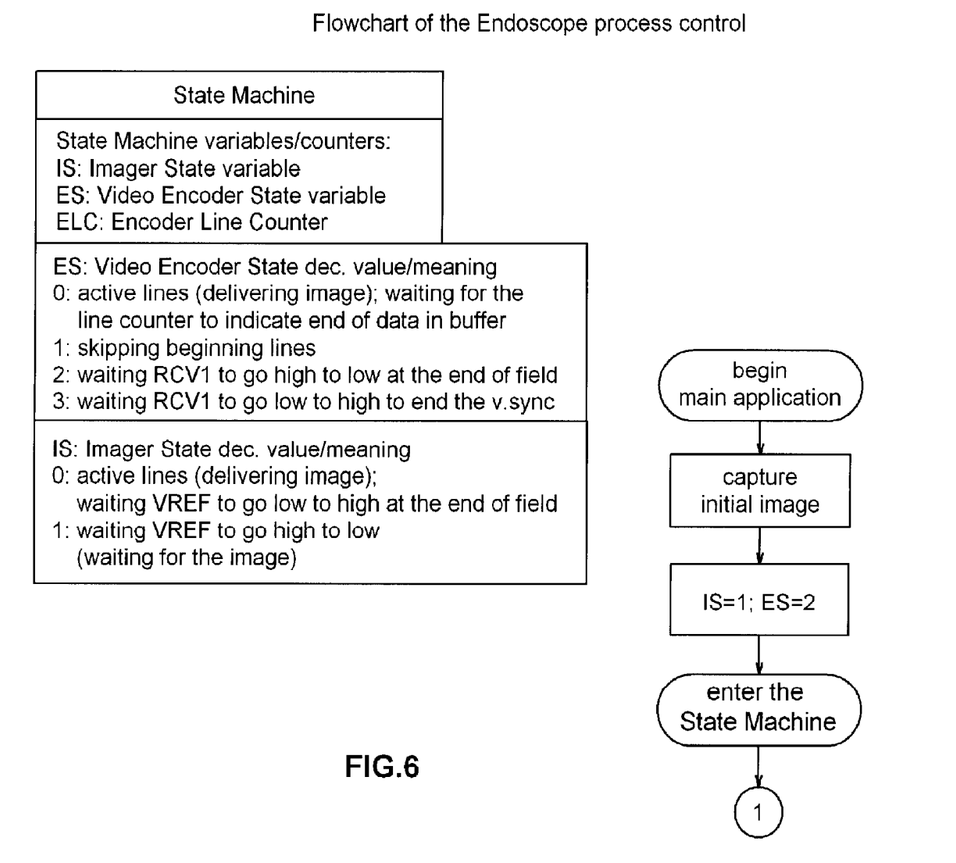
Figure 7:
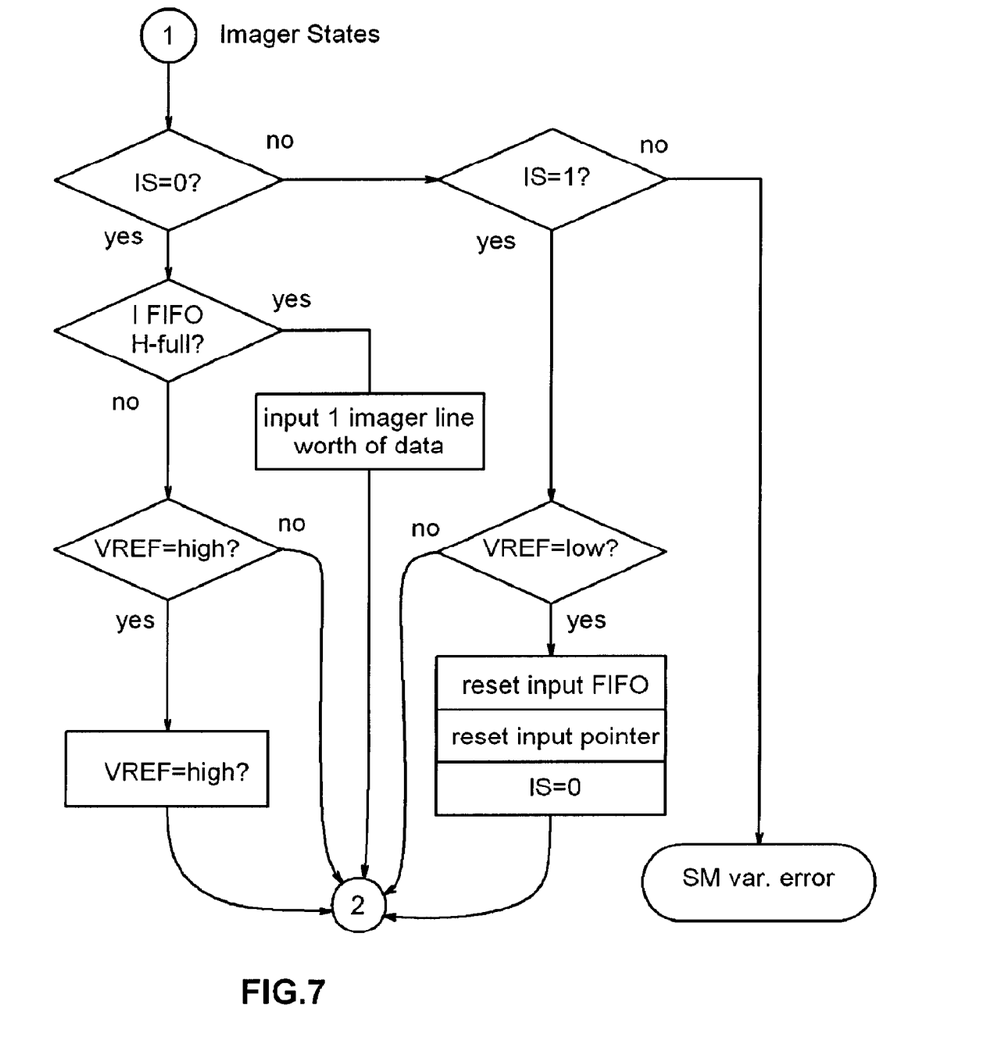
Figure 8:
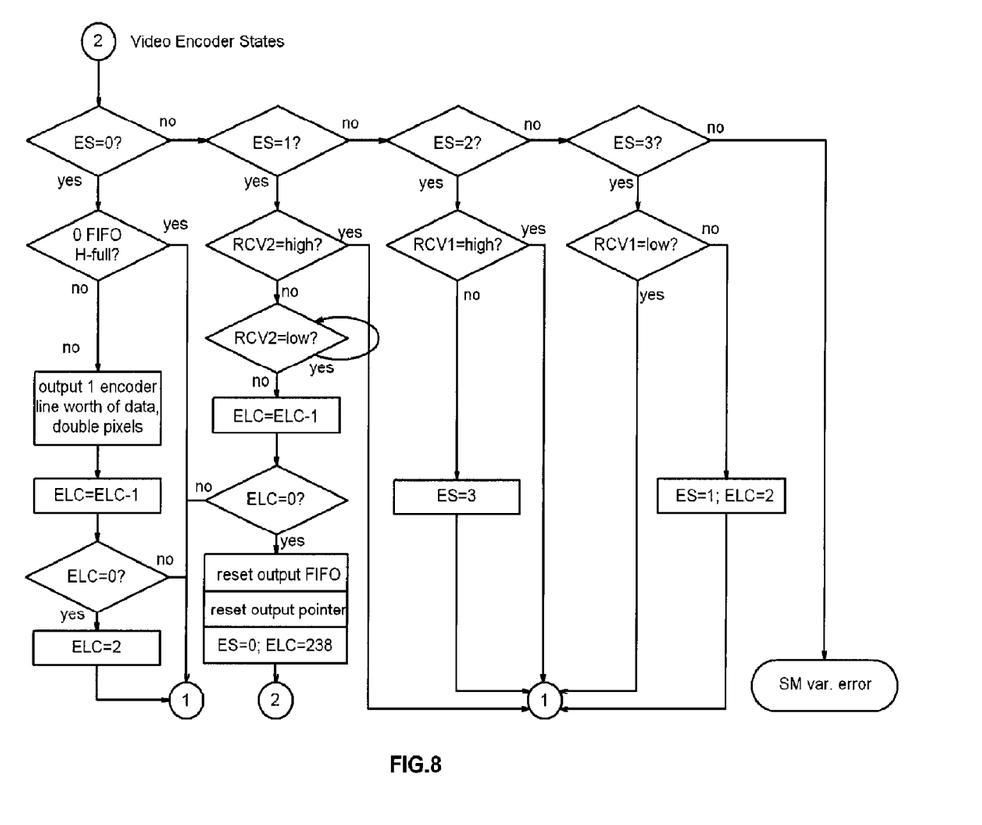

The Electronic Hardware Block Diagram presented on the FIG. 4 illustrates a practical way of building a portable low cost endoscope powered just by a small battery cell(s).

On power up, Battery Monitor 39 indicates the charged or discharged state of the main battery pack. If the battery has sufficient charge, DSP Controller 34 starts and reads Program Flash 35 where the compiled control program is stored. DSP Controller 34 initializes itself and the hardware. DSP Controller 34 queries and sets up CCD Chipset 24 via Cable Interface 25, resets Input FIFO 26, queries and sets up Video Encoder 30, resets Output FIFO 31, sets Digital Pot 37 to midpoint value or other value stored in Digital Pot 37 or in Program Flash 35. DSP Controller 34 enters the State Machine software loop. The Electronic Hardware acts together with the State Machine software to capture and display the electronic representation of the image seen by the Video Endoscope. CCD Chipset 24 autonomously services the imager and sends data and control signals to Cable Interface 25. Data appears at Input FIFO 26 and is stored there line by line. DSP Controller 34 tests Cable Interface 25 and Input FIFO 26, and if there is enough data available, the DSP Controller 34 transfers a certain amount of video data from the Input FIFO 26 into Data SRAM 27. DSP Controller 34 tests Video Encoder 30 and Output FIFO 31, and if there is enough data available, DSP Controller 34 transfers a certain amount of video data from Data SRAM 27 into Output FIFO 31. Video Encoder 30 autonomously reads video data from Output FIFO 31. Video Encoder 30 converts digital video data into analog video signal suitable for display. Video Amplifier 29 amplifies the analog video signal. LCD Controller 28 receives amplified analog video signal and controls 3.5" TFT LCD 32 where image is displayed for viewing. DSP Controller 34 tests Front Panel Switches 38. If the Video Endoscope operator presses any of Front Panel Switches 38 for the purpose of changing the brightness of the image displayed on 3.5" TFT LCD 32, then DSP Controller 34 operates Digital Pot 37, which controls LCD Controller 28.

The flowchart of the process control presented in the FIGS. 5, 6, 7 and 8 illustrates the way the image, acquired by the image sensor, is being reformatted in the pixel domain and its frame rate modified to meet requirements of the TFT LCD display conforming to the NTSC standard.

The Video Endoscope State Machine is a combination of two sub-state machines (the Imager State Machine and the Video Encoder State Machine), each controlled by its own state variable: the IS, which is the Imager State variable; and ES, which is the Video Encoder State variable.

The Imager sub-State Machine has the following inputs: Input FIFO Half-Full Flag, Imager Vertical Blanking VREF signal (active high).

Imager State variable IS decimal values and meaning:
0: active lines (delivering image), and checking the FIFO Half-Full Flag; waiting VREF to go from low to high at the end of field
1: waiting VREF to go from high to low at the start of new field (waiting for the image)

The Imager State variable initial value is 1.

The Video Encoder sub-State Machine has the following inputs:
Output FIFO Half-Full Flag, Video Encoder Vertical Sync RCV1 signal (active low), Video Encoder Horizontal Blanking RCV2 signal (active high).

Video Encoder State variable ES decimal values and meaning:
0: active lines (delivering image), and checking the FIFO Half-Full Flag; waiting for the line counter to indicate end of data in buffer
1: skipping beginning lines
2: waiting RCV1 to go from high to low at the end of field
3: waiting RCV1 to go from low to high to finish the vertical sync The Video Encoder State variable initial value is 2.

The Video Encoder sub-State Machine has a private variable,
ELC (Encoder Line Counter).

The Imager sub-State Machine has the following logic:
If the Imager State variable is 0 or 1, then branch to perform the operations for that state. If the Imager State variable is any other value, then branch to recover from the Imager State Machine variable error.

Whenever the Imager sub-State Machine finishes its operations, the control is passed to the Video Encoder sub-State Machine.

If the Imager State variable is 0, then test the Input FIFO Half-Full Flag, and if that is active (meaning that the Imager has produced enough output to be removed from the FIFO), then input one Imager line worth of data from the FIFO into the SRAM at the current position of the input pointer; update the input pointer, and finish with the Imager sub-State Machine operations.

If the Input FIFO Half-Full Flag is not active (meaning that the Imager has not yet produced enough output to be removed from the FIFO), then test the Imager Vertical Blanking VREF signal, and only if that is high (meaning that the Imager finished delivering the image and started the non-image period), then change the Imager State variable to 1, and, regardless, finish with the Imager sub-State Machine operations.

If the Imager State variable is 1, then test the Imager Vertical Blanking VREF signal, and only if that is low (meaning that the Imager has just finished the non-image period and started delivering the image), then perform the following: reset the Input FIFO, reset the input pointer, change the Imager State variable to 0, and, regardless, finish with the Imager sub-State Machine operations.

The Video Encoder sub-State Machine has the following logic:
If the Video Encoder State variable is 0, 1, 2, or 3, then branch to perform the operations for that state. If the Video Encoder State variable is any other value, then branch to recover from the Video Encoder State Machine variable error.

Whenever the Video Encoder sub-State Machine finishes its operations, the control is passed to the Imager sub-State Machine.

If the Video Encoder State variable is 0, then test the Output FIFO Half-Full Flag, and if that is not active (meaning that the Video Encoder has removed enough output from the FIFO), then output one Video Encoder line worth of data from the SRAM at the current position of the output pointer into the FIFO (double pixel); update the input pointer, decrement the ELC variable, and finish with the Video Encoder sub-State Machine operations, provided that the new value of the ELC variable is not 0. If the new value of the ELC variable is 0, then change the Video Encoder State variable to 2, and finish with the Video Encoder sub-State Machine operations. If the Output FIFO Half-Full Flag (above) is active, then just finish with the Video Encoder sub-State Machine operations.

If the Video Encoder State variable is 1, then test the Video Encoder Horizontal Blanking RCV2 signal (active high), and if that is high, or active, (meaning that the Video Encoder did not yet start a new line), then finish with the Video Encoder sub-State Machine operations. If the Video Encoder Horizontal Blanking RCV2 signal (active high) is low, or not active, then wait until it becomes active again, decrement the ELC variable, and finish with the Video Encoder sub-State Machine operations, provided that the new value of the ELC variable is not 0. If the new value of the ELC variable is 0, then reset the output FIFO, reset the output pointer, change the Video Encoder State variable to 0, change the ELC variable to 238 (number of lines per Video Encoder field), and restart, not finish, with the Video Encoder sub-State Machine operations.

If the Video Encoder State variable is 2, then test the Video Encoder Vertical Sync RCV1 signal (active low), and if that is high, or not active (meaning that the Video Encoder has not yet reached the end of the field), then finish with the Video Encoder sub-State Machine operations. If the Video Encoder Vertical Sync RCV1 signal is low, or active, then change the Video Encoder State variable to 3, and finish with the Video Encoder sub-State Machine operations.

If the Video Encoder State variable is 3, then test the Video Encoder Vertical Sync RCV1 signal (active low), and if that is low, or active (meaning that the Video Encoder is at the beginning of a new field but has not yet reached the end of the sync), then finish with the Video Encoder sub-State Machine operations. If the Video Encoder Vertical Sync RCV1 signal is high, or not active, then change the Video Encoder State variable to 1, change the ELC variable to 2 (number of lines to skip at the top of the Video Encoder field), and finish with the Video Encoder sub-State Machine operations.

The disclosed control process makes possible to run the image sensor in the reduced frame rate, yet display the acquired image on the LCD monitor with the standard TV frame rate. Simultaneously, the conflict between the number of horizontal pixels and vertical lines of the image sensor and LCD display monitor is resolved.

I claim:

1. A digital imaging probe comprising: an image sensor in a micro ball grid array packaging, a wide angle imaging lens positioned in front of a sensitive area of the image sensor, an LED illuminator positioned in the space in front of a storage area of the image sensor and next to the imaging lens, an optically clear window positioned immediately in front of both the lens and the LED illuminator, a light blocking separator positioned between the lens and the LED illuminator, a flexible circuit carrying the image sensor and having an extension, with the LED on its tip on one end and the multi pin connector on the other end, a cylindrical enclosure that holds all the above elements together in their relative positions and is impermeably connected to a flexible sleeve that encloses the flexible circuit.

2. The digital imaging probe according to claim 1 wherein the cylindrical enclosure has a diameter at a distal end of no larger than 6 mm.

3. The digital imaging probe according to claim 1 where the flexible circuit is a single layer type with cold rolled copper traces.

4. The digital imaging probe according to claim 1 where the flexible circuit is a dual layer type with cold rolled copper traces.

5. The digital imaging probe according to claim 1 where the LED illuminator is a single white LED consuming less than 100 mW of power.

6. The digital imaging probe according to claim 1 where the imaging lens is a wide angle lens with the full view angle no less than 90 degrees and no more than 120 degrees.

7. The digital imaging probe according to claim 1, wherein the image sensor is selected from the group consisting of a CCD image sensor and a CMOS image sensor.

8. The digital imaging probe according to claim 1, wherein the image sensor is a CCD frame transfer type image sensor.

9. A digital imaging probe having a cylindrical enclosure and comprising: an image sensor having a sensitive area and a storage area, a wide angle imaging lens positioned in front of the sensitive area of the image sensor, an LED illuminator positioned in the space in front of the storage area of the image sensor and next to the imaging lens, an optically clear window positioned immediately in front of both the lens and the LED illuminator, having an inner surface, a light-impermeable separator positioned between the lens and the LED illuminator, and extending to the inner surface of the window, a flexible electrical circuit having a first end in electrical communication with the image sensor and with the LED, and having a second end consisting of an electrical coupling.

10. The digital imaging probe according to claim 9, wherein the image sensor is selected from the group consisting of a CCD image sensor and a CMOS image sensor.

11. The digital imaging probe according to claim 9 wherein the cylindrical enclosure has a diameter no larger than 6 mm.

12. The digital imaging probe according to claim 9, wherein the flexible circuit is a dual layer type with cold rolled copper traces.

13. The digital imaging probe according to claim 9 where the LED illuminator is a single white LED consuming less than 100 mW of power.

14. The digital imaging probe according to claim 9 where the imaging lens is a wide angle lens with the full view angle no less than 90 degrees and no more than 120 degrees.

15. A portable endoscope suitable for aiding during endotracheal intubation comprising the three modules: a digital imaging probe module comprising the digital imaging probe according to claim 9, an in-line probe controller module, and a display and control module.

16. The portable endoscope according to claim 15, where the in-line probe controller module is connected with the digital imaging probe module on one side and with the display and supply module on the other side; its distance from the imaging sensor is no closer than 10 inches and from the display and supply module no longer than 30 inches.

17. The portable endoscope according to claim 15, where the display and supply module comprises a power supply, a video display, and an image rescaling processor that converts both the temporal frame rate and the spacial resolution of the pixelated electronic image outputted by the in-line probe controller to be compatible with the NTSC or PAL video display requirements.

* * * * *